(12) United States Patent
Pugh

(10) Patent No.: US 8,996,697 B2
(45) Date of Patent: Mar. 31, 2015

(54) SERVER AUTHENTICATION

(76) Inventor: Rhoderick John Kennedy Pugh, Woking (GB)

( * ) Notice: Subject to any disclaimer, the term of this patent is extended or adjusted under 35 U.S.C. 154(b) by 485 days.

(21) Appl. No.: 13/159,140

(22) Filed: Jun. 13, 2011

(65) Prior Publication Data

US 2011/0247053 A1    Oct. 6, 2011

Related U.S. Application Data

(63) Continuation of application No. 11/573,980, filed as application No. PCT/GB2005/003237 on Aug. 19, 2005, now abandoned.

(51) Int. Cl.
*H04L 29/06* (2006.01)
*G06Q 30/00* (2012.01)
*H04L 29/12* (2006.01)
(Continued)

(52) U.S. Cl.
CPC ............ *H04L 63/1441* (2013.01); *G06Q 30/00* (2013.01); *H04L 61/2503* (2013.01); *A61L 2/10* (2013.01); *G06Q 10/107* (2013.01); *H04L 29/12584* (2013.01); *H04L 29/12349* (2013.01); *H04L 61/157* (2013.01); *G06F 2221/2119* (2013.01); *G06F 2221/2149* (2013.01); *H04L 29/12066* (2013.01); *H04L 61/1511* (2013.01); *H04L 63/1466* (2013.01); *H04L 63/1483* (2013.01); *H04L 2463/102* (2013.01); *Y10S 707/99931* (2013.01)
USPC ............... 709/225; 709/206; 709/207; 707/1; 707/999.001; 726/10; 726/4; 713/201

(58) Field of Classification Search
CPC ........ G06Q 30/00; G06Q 10/107; A61L 2/10; H04L 29/12349; H04L 29/12584; H04L 63/1441
USPC ............... 709/225, 206, 207; 707/1, 999.001; 726/10, 4
See application file for complete search history.

(56) References Cited

U.S. PATENT DOCUMENTS

| | | | | |
|---|---|---|---|---|
| 6,654,891 | B1 * | 11/2003 | Borsato et al. | 726/6 |
| 6,865,671 | B1 * | 3/2005 | Assmann | 713/154 |
| 6,928,167 | B1 * | 8/2005 | Maeda et al. | 380/285 |

(Continued)

FOREIGN PATENT DOCUMENTS

WO    WO 2006018647 A1 *    2/2006

OTHER PUBLICATIONS

Hutchinson, "Study of Denial of Service", 2003.*

(Continued)

*Primary Examiner* — O. C. Vostal
(74) *Attorney, Agent, or Firm* — Michael J. Donohue; Davis Wright Tremaine LLP

(57) ABSTRACT

A method of authenticating a content-provider server, the method comprising: determining a domain name of the content-provider server; obtaining a fragment of a database of IP addresses, the fragment corresponding to the domain name of the content-provider server and storing one or more IP addresses associated with the domain name; comparing the IP address of the content-provider server against the IP addresses of the fragment; and providing an indication that the IP address of the content-provider server is included or excluded from the fragment of IP addresses. Additionally, a client computer and server operable to implement the method are described.

16 Claims, 6 Drawing Sheets

(51) Int. Cl.
 *A61L 2/10* (2006.01)
 *G06Q 10/10* (2012.01)

(56) References Cited

U.S. PATENT DOCUMENTS

| | | | |
|---|---|---|---|
| 6,947,909 B1* | 9/2005 | Hoke, Jr. | 705/54 |
| 7,072,944 B2* | 7/2006 | Lalonde et al. | 709/206 |
| 7,308,709 B1* | 12/2007 | Brezak et al. | 726/10 |
| 7,409,544 B2* | 8/2008 | Aura | 713/162 |
| 7,437,482 B2* | 10/2008 | Jungck | 709/246 |
| 7,457,823 B2* | 11/2008 | Shraim et al. | 1/1 |
| 7,523,173 B2* | 4/2009 | Seki et al. | 709/219 |
| 8,106,764 B2* | 1/2012 | Hershkovitz et al. | 340/531 |
| 2002/0064149 A1* | 5/2002 | Elliott et al. | 370/352 |
| 2002/0161745 A1* | 10/2002 | Call | 707/1 |
| 2003/0055979 A1* | 3/2003 | Cooley | 709/227 |
| 2004/0006621 A1 | 1/2004 | Bellinson et al. | |
| 2004/0054810 A1* | 3/2004 | Furukawa et al. | 709/249 |
| 2004/0193875 A1* | 9/2004 | Aura | 713/162 |
| 2004/0267886 A1* | 12/2004 | Malik | 709/206 |
| 2005/0125692 A1* | 6/2005 | Cox et al. | 713/201 |
| 2005/0278775 A1* | 12/2005 | Ross | 726/2 |
| 2006/0212930 A1* | 9/2006 | Shull et al. | 726/10 |
| 2006/0212931 A1* | 9/2006 | Shull et al. | 726/10 |
| 2009/0144442 A1* | 6/2009 | Zheng et al. | 709/236 |
| 2010/0309784 A1* | 12/2010 | Mihaly et al. | 370/230 |
| 2010/0325714 A1* | 12/2010 | Iyer et al. | 726/8 |
| 2012/0131332 A1* | 5/2012 | Lin | 713/155 |

OTHER PUBLICATIONS

Pugh, "Internet Security System", PCT/GB05/003237, Aug. 2005.*
Eastlake D., "Domain Name System Security Extensions," IETF Standard, Internet Engineering Task Force, Mar. 1999, XP015008318.
Felten E. W., et al., "Web Spoofing: An Internet Con Game," Software World, A.P. Publications, No. 540-96, Mar. 1997, XP002290150.
Loftesness, S., et al. "Responding to Phishing Attacks: a Glenbrook ActionMap," Announcement Glenbrooks, Jan. 2004, XP002307182.
Chen Ding et al., "Centralized Content-Based Web Filtering and Blocking: How Far Can it Go"? Systems, Man and Cybernetics, 1999, IEEE SMC '99 Conference Proceedings.
Alvey R. et al., "The Art of Web Filtering," SANS Institute, GSEC Practical V1 4B, Feb. 9, 2004.

* cited by examiner

| | 7 | 8 | 9 |
|---|---|---|---|
| 19 — Onlinebank.com | 200.1.1.1 | | |
| | 200.1.2.3 | 21 Aug 2004 | |
| | 200.1.7.49 | | |
| | 200.1.7.50 | | |
| | 200.1.7.54 | onlinebank.jpg | |
| | 200.1.20.3 | | |
| | 200.1.74.6 | | |
| | 200.1.200.4 | www.nationalreg.org/Idetails?=onlinebank | |
| 18 — | 200.1.222.8 | | |
| | | | |
| | | | |

Figure 8

SERVER AUTHENTICATION

The present invention relates to a method and system for authenticating servers of content-providers that provide content-data, such as webpage data, to client computers over a communications network, such as the Internet.

As online banking and other transactions of value have increased in popularity over the Internet, users have been fooled or coerced into revealing bank account details, passwords and other personal details to unauthorised people who may use this information dishonestly. This technique, often now referred to as "phishing" may be initiated from an e-mail supposedly from a bank or other financial or commercial institution, such as an e-trader, sent to an ostensible customer with a link to a website where there is a request to enter personal or bank details, passwords or PIN numbers. This website may be an exact copy of a valid site belonging to the correct financial or commercial institution, or may be an entirely valid site of such institution with a fraudulent pop-up window that requests details or uses other means to deceive the customer concerned.

Other phishing methods include inserting rogue computer code or object into legitimate pages by methods, which include proxy servers, packet manipulation and installation of software or devices on a client computer. It has also been known for fraudsters to adopt similar URL's (uniform resource locators) to a genuine business to fool people into thinking they are on a legitimate site. For example, the URL 0nlinebank.com, with an initial "0" (zero) rather than an initial "O" may be used to deceive people into believing they have reached the site of Onlinebank.com.

Still further methods include setting up totally fraudulent web sites pretending to be legitimate or non-existent charities or commercial organisations to fool users into donating monies to or purchasing goods from fraudulent organisations, which have not necessarily been reached via invitation from e-mails.

Numerous prior proposals have been made with a view to improving security on the Internet and avoiding or frustrating phishing, but none have been entirely satisfactory.

For example, WO 2004/055632 describes a system in which a complex algorithm is employed to determine whether a particular URL may be trusted or not. This analysis may take account of content and layout of a web page, age and size of the website and the number of hyperlinks and scores the web page under each of these headings to give a determination as to whether the web page can likely be trusted or likely not be trusted. On the basis of this analysis, the URL of the web page is added to a trusted list or a distrusted list maintained by the client computer. Nevertheless, a fraudulent website will often appear as an exact copy of a legitimate site and therefore be added to the list of trusted sites.

In a first aspect, the present invention provides a method of authenticating a content-provider server comprising: determining a domain name of the content-provider server; obtaining a fragment of a database of IP addresses, the fragment corresponding to the domain name of the content-provider server and storing one or more IP addresses associated with the domain name; comparing the IP address of the content-provider server against the IP addresses of the fragment; and providing an indication that the IP address of the content-provider server is included or excluded from the fragment of IP addresses.

Preferably, the fragment is stored on a remote server and obtaining the fragment comprises requesting from the server a copy of the fragment and receiving from the server a copy of the fragment.

Advantageously, the fragment is stored on the server as a file having a filename that is unique to the domain name of the content-provider server and requesting a copy of the fragment from the server comprises requesting a file having a filename that is unique to the domain name of the content-provider server.

Conveniently, the filename of the fragment is unique to both the domain name of the content-provider server and a domain name of the server on which the fragment is stored.

Preferably, the filename of the fragment is encrypted using encryption keys derived from the domain name of the content-provider server and the domain name of the server on which the fragment is stored.

Advantageously, the fragment stores one or more authenticated IP addresses and one or more non-authenticated IP addresses and the method comprises providing an indication that the IP address of the content-provider server is an authenticated IP address, a non-authenticated IP address, or neither.

Conveniently, the method comprises: storing a database of authenticated IP addresses and a database of non-authenticated IP addresses; appending the IP addresses of the fragment to at least one of the database of authenticated IP addresses and the database of non-authenticated IP addresses; comparing the IP address of the content-provider server against the database of authenticated IP addresses and the database of non-authenticated IP addresses; and providing an indication that the IP address of the content-provider server is an authenticated IP address, a non-authenticated IP address, or neither.

Preferably, the method comprises: obtaining a list of non-authenticated IP addresses from a remote server; and comparing the IP address of the content-provider server against the IP addresses of the fragment and the list of non-authenticated IP addresses.

Advantageously, the method comprises: storing a database of authenticated IP addresses and a database of non-authenticated IP addresses; appending the IP addresses of the fragment to at least one of the database of authenticated IP addresses and the database of non-authenticated IP addresses; appending the list of non-authenticated IP addresses to the database of non-authenticated IP addresses; comparing the IP address of the content-provider server against the database of authenticated IP addresses and the database of non-authenticated IP addresses; and providing an indication that the IP address of the content-provider server is an authenticated IP address, a non-authenticated IP address, or neither.

Conveniently, the content-provider server has a hostname and the method comprises: obtaining first data from the hostname; resolving the IP address of the hostname; obtaining second data from the resolved IP address; comparing the first data and second data; and providing an indication that the first data and second data are identical or non-identical.

Preferably, the fragment includes one or more URLs or portions of URLs associated with each IP address stored by the fragment, and the method comprises: comparing at least a portion of the URL of the content-provider server against the URLs or portions of URLs of the fragment that are associated with the IP address of the content-provider server; and providing an indication that the IP address and the portion of the URL of the content-provider server is included in or excluded from the fragment.

In a second aspect, the present invention provides a client computer connectable to a content-provider server over a communications network, wherein the client computer is operable to: determine a domain name of the content-provider server; obtain a fragment of a database of IP addresses, the fragment corresponding to the domain name of the content-provider server and storing one or more IP addresses associated with the domain name; compare the IP address of the content-provider server against the IP addresses of the fragment; and provide an indication that the IP address of the content-provider server is included or excluded from the IP addresses of the fragment.

Preferably, the client computer is operable to request data from the content-provider server and to obtain the fragment in response to the request for data from the content-provider server.

Advantageously, the client computer is operable to: request data from the content-provider server; determine whether data from the content-provider server has previously been requested; and to obtain the fragment if data from the content-provider has not previously been requested.

Conveniently, the client computer is operable to retrieve the fragment from a server over the communications network, and the fragment is stored on the server as a file having a filename that is unique to the domain name of the content-provider server.

Preferably, the fragment is stored on a security server.

More preferably, the client computer is operable to determine whether the fragment of IP addresses stored on the server has changed and to retrieve from the server the fragment if it is determined that the fragment has changed.

Advantageously, the filename of the fragment is unique to both the domain name of the content-provider server and a domain name of the server on which the fragment is stored.

Conveniently, the filename of the fragment is encrypted using encryption keys derived from the domain name of the content-provider server and the domain name of the server on which the fragment is stored.

Preferably, the fragment stores one or more authenticated IP addresses and one or more non-authenticated IP addresses and the client computer is operable to provide an indication that the IP address of the content-provider server is an authenticated IP address, a non-authenticated IP address, or neither.

Advantageously, the client computer stores a database of authenticated IP addresses and a database of non-authenticated IP addresses, and the client computer is operable to: append the IP addresses of the fragment to at least one of the database of authenticated IP addresses and database of non-authenticated IP addresses; compare the IP address of the content-provider server against the database of authenticated IP addresses and the database of non-authenticated IP addresses; and provide an indication that the IP address of the content-provider server is an authenticated IP address, a non-authenticated IP address, or neither.

Conveniently, the client computer is connectable to a security server over the communications network, and the client computer is operable to obtain a list of non-authenticated IP addresses from the security server and to the compare the IP address of the content-provider server against the IP addresses of the fragment and the list of non-authenticated IP addresses.

Preferably, the client computer stores a database of authenticated IP addresses and a database of non-authenticated IP addresses, and the client computer is operable to: append the IP addresses of the fragment to at least one of the database of authenticated IP addresses and database of non-authenticated IP addresses; append the list of non-authenticated IP addresses to the database of non-authenticated IP addresses; compare the IP address of the content-provider server against the database of authenticated IP addresses and the database of non-authenticated IP addresses; and provide an indication that the IP address of the content-provider server is an authenticated IP address, a non-authenticated IP address, or neither.

Advantageously, the client computer is operable to: obtain data from the content-provider server that includes a link to a further content-provider server; compare the IP address of the further content-provider server against the IP addresses of the fragment, and provide an indication that the IP address of the further content-provider server is included or excluded from the received database of IP addresses.

Conveniently, the content-provider server has a hostname and the client computer is operable to: obtain first data from the hostname; resolve the IP address of the hostname; obtain second data from the resolved IP address; compare the first data and second data; and provide an indication that the first data and second data are identical or non-identical.

Preferably, the fragment includes one or more URLs or portions of URLs associated with each IP address stored by the fragment, and the client computer is further operable to: compare at least a portion of the URL of the content-provider server against the URLs or portions of URLs of the fragment that are associated with the IP address of the content-provider server; and provide an indication that the IP address and the portion of the URL of the content-provider server is included in or excluded from the fragment.

Preferably, the fragment stores IP addresses associated with a URL.

Advantageously, the client computer is operable to provide a visual indication that the content-provider server is a trusted or non-trusted site.

Conveniently, the client computer operates a window-based operating system and the client computer is operable to determine whether an active window of the operating system is executing an application capable of requesting data from the content-provider server, and the client computer is operable to compare the IP address of the content-provider server and to provide an indication that the IP address of the content-provider server is included or excluded from the IP addresses of the fragment if it is determined that an active window is executing an application capable of requesting data from a content-provider server.

In a third aspect, the present invention provides a method of operating a client computer connectable to a content-provider server over a communications network, the method comprising: determining a domain name of the content-provider server; obtaining a fragment of a database of IP addresses, the fragment corresponding to the domain name of the content-provider server and storing one or more IP addresses associated with the domain name; comparing the IP address of the content-provider server against the IP addresses of the fragment; and providing an indication that the IP address of the content-provider server is included or excluded from the IP addresses of the fragment.

In a fourth aspect, the present invention provides a computer program or suite of computer programs, which may be provided on a computer-readable storage medium, executable by a client computer to perform the above method.

In a fifth aspect, the present invention provides a security server connectable to a client computer over a communications network, the security server storing a database of IP addresses as a plurality of fragments, each fragment corresponding to a domain name and storing IP addresses associated with the domain name, and the security server is operable to receive a request from the client computer for a fragment, and to deliver the requested fragment to the client computer.

Preferably, the security server stores each fragment as a file having a filename that is unique to the domain name to which the fragment corresponds, and the security server is operable to receive a request from the client computer for a fragment having a particular filename, and to deliver the fragment having the particular filename to the client computer.

Advantageously, the filename of the fragment is unique to both the domain name to which the fragment corresponds and to a domain name of the security server on which the fragment is stored.

Conveniently, the filename of the fragment is encrypted using encryption keys derived from the domain name to which the fragment corresponds and the domain name of the server on which the fragment is stored.

Preferably, the security server is connectable to a content-provider server over the communications network and the security server is operable to: receive one or more IP addresses from the content-provider server; and store the received IP addresses as a fragment, the fragment corresponding to a domain name of the content-provider server.

Advantageously, the security server stores a database of authenticated IP addresses and a database of non-authenticated IP addresses as a plurality of fragments.

Conveniently, the security server stores a database of authenticated IP address as a plurality of fragments, each fragment corresponding to a domain name and storing authenticated IP addresses associated with the domain name, and a database of non-authenticated IP addresses, and the security server is operable to: receive a request from the client computer for a fragment of the database of authenticated IP addresses; deliver the requested fragment to the client computer; receive a request from the client computer for the database of non-authenticated IP addresses; and deliver the database of non-authenticated IP addresses to the client computer.

Preferably, the security server is operable to receive a request from the client computer that includes information identifying a domain name of a content-provider server, and to deliver to the client computer a fragment corresponding to the identified domain name.

Advantageously, each fragment stores IP addresses associated with a URL.

In a sixth aspect, the present invention provides a method of operating a security server connected to a client computer over a communications network, the method comprising: storing a database of IP addresses as a plurality of fragments, each fragment corresponding to a domain name and storing IP addresses associated with the domain name; receiving a request from the client computer for a fragment; and delivering the requested fragment to the client computer.

In a seventh aspect, the present invention provides a computer program or suite of computer programs, which may be provided on a computer-readable storage medium, executable by a server computer to perform the above method.

In an eighth aspect, the present invention provides a client computer connectable to a content-provider server and to a security server over a communications network, the security server storing a database of IP addresses as a plurality of fragments, each fragment corresponding to a domain name and storing IP addresses associated with the domain name, and the client computer is operable to: determine the domain name of the content-provider server; obtain from the security server a fragment of the database of IP addresses corresponding to the domain name of the content-provider server; compare the IP address of the content-provider server against the received fragment of IP addresses; and provide an indication that the IP address of the content-provider server is included or excluded from the received fragment of IP addresses.

The term 'window-based operating system' as used herein is intended to encompass any operating system that makes use of windows in a graphic display, usually only one such window being active at any one time, and sometimes only one such window being visible on a graphic display at any one time. Examples of window-based operating systems include Microsoft Windows®, the various Macintosh® operating systems, as well as a variety of other window-based operating systems employed by various hand-held computer devices and third and higher generation mobile phones.

Highly sophisticated fraudsters have been known to engage in what is known as "IP address spoofing". In this case, even when a webpage is sent to the client computer and the IP address has been checked and may be found to be an authenticated IP address, it may still be possible for a fraudulent site to have produced it. This is because it is possible to configure a web server to send information that appears to emanate from a different IP address to the one it actually comes from. However, this possibility can be readily overcome. If the apparently authenticated IP address is sent in substitution for the hostname or domain-name part of the URL, the apparently validated IP address can be authenticated for certain. If the same or similar content-data (e.g. webpage data) is returned then it follows that the content-data has come from a certainly authenticated IP address. If no reply is received or a totally different reply, then it can readily be surmised that the original content-data did not originate from the apparently authenticated IP address but from an altogether different fraudulent site. In this case, a danger warning should be given to override any other indication that might otherwise seem appropriate.

In order that the present invention may be more readily understood, embodiments thereof will now be described, by way of example, with reference to the accompanying drawings in which:

FIG. 8 is a schematic diagram of an alternative database stored on a security server embodying the present invention.

Figure 1:
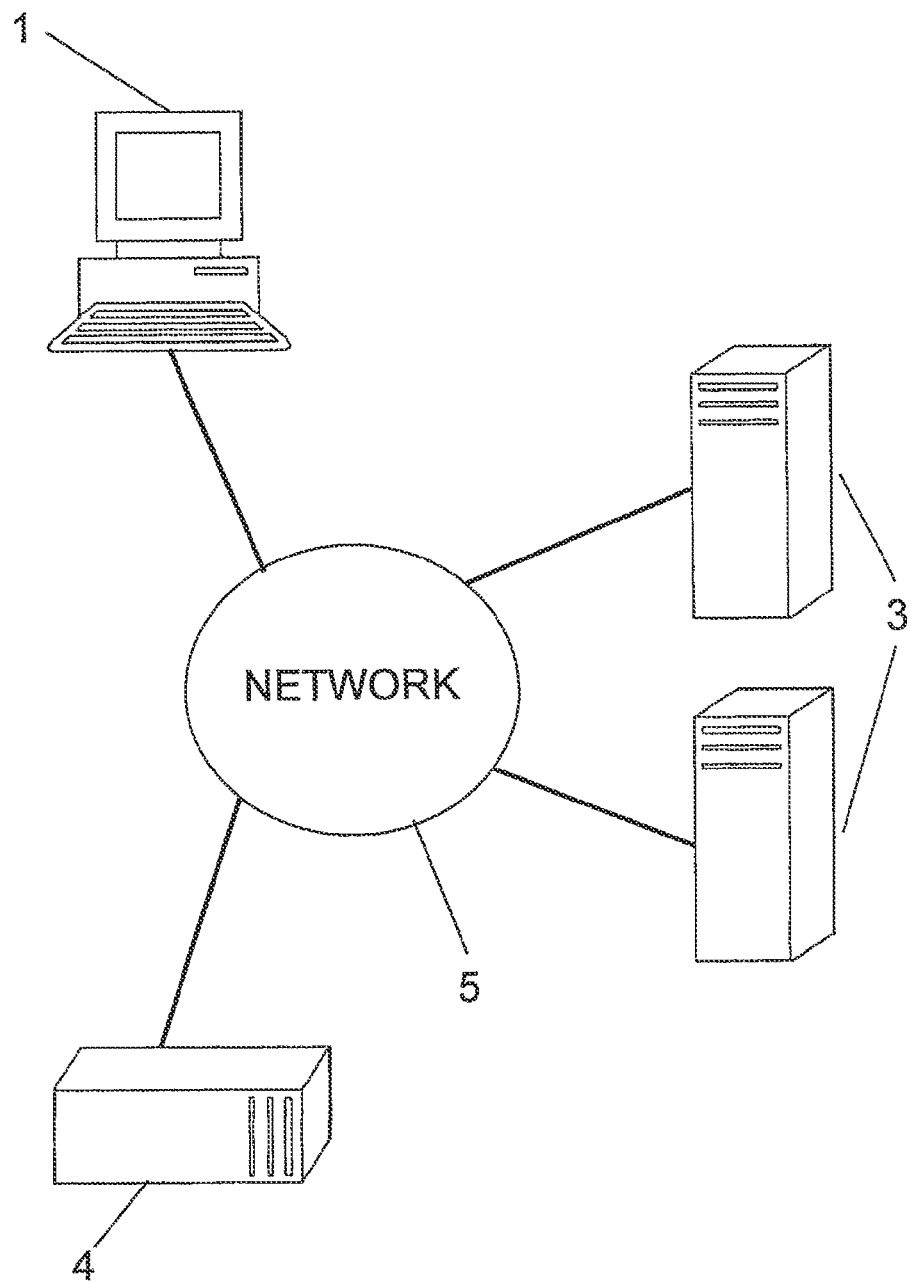
FIG. 1 is a schematic representation of a computer network.

FIG. 1 shows the basic arrangement of a network, such as the Internet, in which a client computer 1 is connected to a plurality of content-provider servers 3 and to a security server 4 over a communications network 5.

Each content-provider server 3 has at least one IP address and stores content-data, such as HTML files, Java applets, sound and image files, etc., for downloading by the client computer 1. The present invention is particularly concerned with content-provider servers 3 that require user authorisation from the client computer 1. For example, the content-provider server 3 may be an online bank, and content-data relating to a particular account holder, such as a statement of account, is provided only upon receipt from the client computer of a username and password. Alternatively, the content-provider server may be an online shop, whereupon goods may be purchased only upon receipt of the purchaser's credit or debit card details.

The content-data of a content-provider server 3 is generally accessed by way of a uniform resource locator (URL), e.g. www.onlinebank.com/home/login.shtml. The URL comprises a hostname and a path or filename, which in the present example are 'www.onlinebank.com' and '/home/long.shtml' respectively. The hostname comprises a domain name, such as a fully qualified domain name or a sub-domain. URLs and IP addresses are related but are not directly equivalent to each other. Thus, when a web browser requests content-data from the URL www.onlinebank.com/home/login.shtml, a domain name server (DNS) looks up and converts the hostname part of the URL into an IP address, such as 207.46.250.222 or whatever the appropriate IP address may be. Owing to domain-name aliasing, different hostnames may point to the same IP address. For example, www.onlinebank.co.uk or www.onlinebank.net may point to the same IP address as that of www.onlinebank.com. Moreover, stealth redirection means that a user accessing the same URL may be redirected to a different IP address on different occasions, even though the same hostname appears in the URL. Consequently, a user requesting content-data from a content-provider server 3, e.g. by entering a URL into his web browser, is generally unaware of the actual IP address and thus the actual server 3 providing the content-data.

Figure 2:
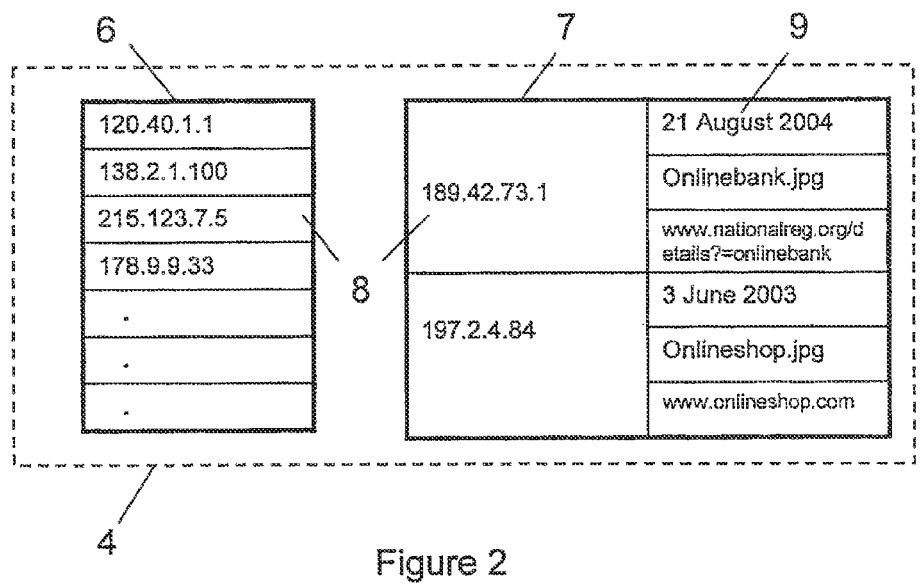
FIG. 2 is a schematic diagram of databases stored on a security server embodying the present invention.

As shown in FIG. 2, the security server 4 stores a database of non-authenticated IP addresses 6 and preferably a database of authenticated IP addresses 7. Each database 6, 7 comprises a list of IP addresses 8. Additionally, the databases 6,7 may store related-information 9 associated with each of the listed IP addresses, such as the date on which the IP address was entered or updated in the database, and the level of threat or authenticity associated with the IP address. For example, the IP addresses of a content-provider server 3 that is known to mimic an online bank may have a high threat level, whilst an online shop that does not appear to satisfy certain online security requirements may have a low threat level. The related-information 9 associated with a particular IP address may also include details of the authority or subscriber that provided the IP address, as well as a graphical image (e.g. logo or animation) or sound clip associated with the authority or subscriber. Furthermore, the related-information 9 may include one or more links associated with a particular IP address. For example, each database 6, 7 might store a set of URL links to websites that are promoted in response to a user accessing a particular content-provider server. Additionally, each database 6,7 might store a set of URL links to other content-provider servers (e.g. websites) that provide information about a subscriber, not necessarily provided by the subscriber, such as company profile, consumer information, credit rating, market analysis, share price, etc. Accordingly, a user is presented with one or more secure links to content-provider servers that provide independent information regarding a particular subscriber/content-provider.

The database of non-authenticated IP addresses 6 lists IP addresses that have been identified as fraudulent or potentially insecure, i.e. the database 6 lists IP addresses of content-provider servers 3 that are not to be trusted. It is preferred that non-authenticated IP addresses be provided to the security server 4 by an organisation of assured status and integrity, such as a police authority or other government authority responsible for monitoring fraud, a banking authority, or other authoritative body outside of the commercial control of the security provider responsible for the security server 4.

In a particular embodiment, a single assured organisation is responsible for maintaining the non-authenticated database 6. The assured organisation may deliver the entire database 6, or portions of the database 6 that have changed, to the security server 4. Alternatively, the security server 4 may retrieve the entire database 6, or portions of the database 6 that have changed, from the assured organisation. Delivery or retrieval may occur periodically or whenever a change occurs to the database 6.

In an alternative embodiment, several assured organisations are responsible for maintaining the non-authenticated database 6. In this instance, each assured organisation provides a portion of the non-authenticated database 6 stored on the security server 4. Each portion may be delivered to the security server 4 by the assured organisation, or the security server 4 may retrieve the portion from the assured organisation at periodic intervals.

The database of authenticated IP addresses 7 lists those IP addresses that have been provided by subscribers to the security server 4. Each subscriber is typically a content-provider that wishes to register its servers on the security server 4. For example, the subscriber may be the company OnlineBank, which provides a list of all its IP addresses. Each subscriber provides a portion of the authenticated database 6, which may be delivered to the security server 4 by the assured organisation, or the security server 4 may retrieve the portion from the subscriber at periodic intervals.

In a particular embodiment, the subscriber may also provide a list of IP addresses that it regards as untrustworthy and should therefore be added to the database of non-authenticated IP addresses 6. However, maintenance of the database of non-authenticated IP addresses 6 is preferably carried out by assured organisations only.

Figure 3:
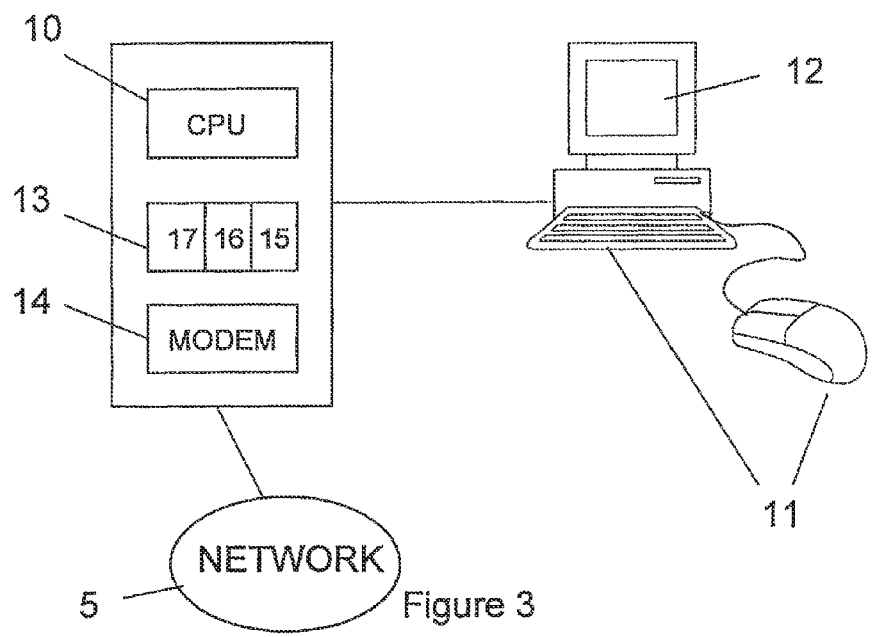
FIG. 3 is a schematic diagram of a client computer embodying the present invention.

The client computer 1, as illustrated in FIG. 3 comprises a processor 10 provided with a window-based operating system, a user-input device 11 (such as a keyboard and/or mouse), a visual display unit (VDU) 12, a memory 13 and a modem 14 for transferring data across the communications network 5. The client computer 1 may alternatively transfer data across the communications network 5 via a LAN, whereby the client computer 1 includes an ethernet card or similar device (not shown) for transferring data over the LAN, or indeed any other means for transferring data from the client computer 1 across the communications network 5.

The client computer 1 preferably includes a web-browser (e.g. as part of the operating system or stored separately in memory 13) for receiving content-data from the content-provider servers 3. However, any application-software suitable for receiving content-data from a content-provider server 3 (e.g. a file-browser or e-mail client operating in http, https, ftp, or similar protocol) may equally be used. Preferably, the web-browser or application-software is suitable for receiving user-authorisation data from the user-input device 11 and for transferring the user-authorisation data to a content-provider server 3.

The memory 13 stores a server-authentication application 15, which is executable by the processor 10. The server-authentication application 15 includes instructions for receiving (e.g. downloading) from the security server 4 the entire non-authenticated database 6 and preferably the entire authenticated database 7. The server-authentication application 15 preferably provides the user with the opportunity to receive new, updated or refreshed databases 6,7 from the security server 4 automatically, periodically without intervention of the user of the client computer 1, or by connection to the security server 4 at specified intervals or at times entirely at the option of the user. The received databases are then stored in memory 13. For the purposes of clarity, the databases stored on the client computer 1 shall be referred to hereafter as the client-database of non-authenticated IP addresses 16 (or alternatively the non-authenticated client-database) and the client-database of authenticated client database 17 (or alternatively the authenticated client-database).

Figure 4:
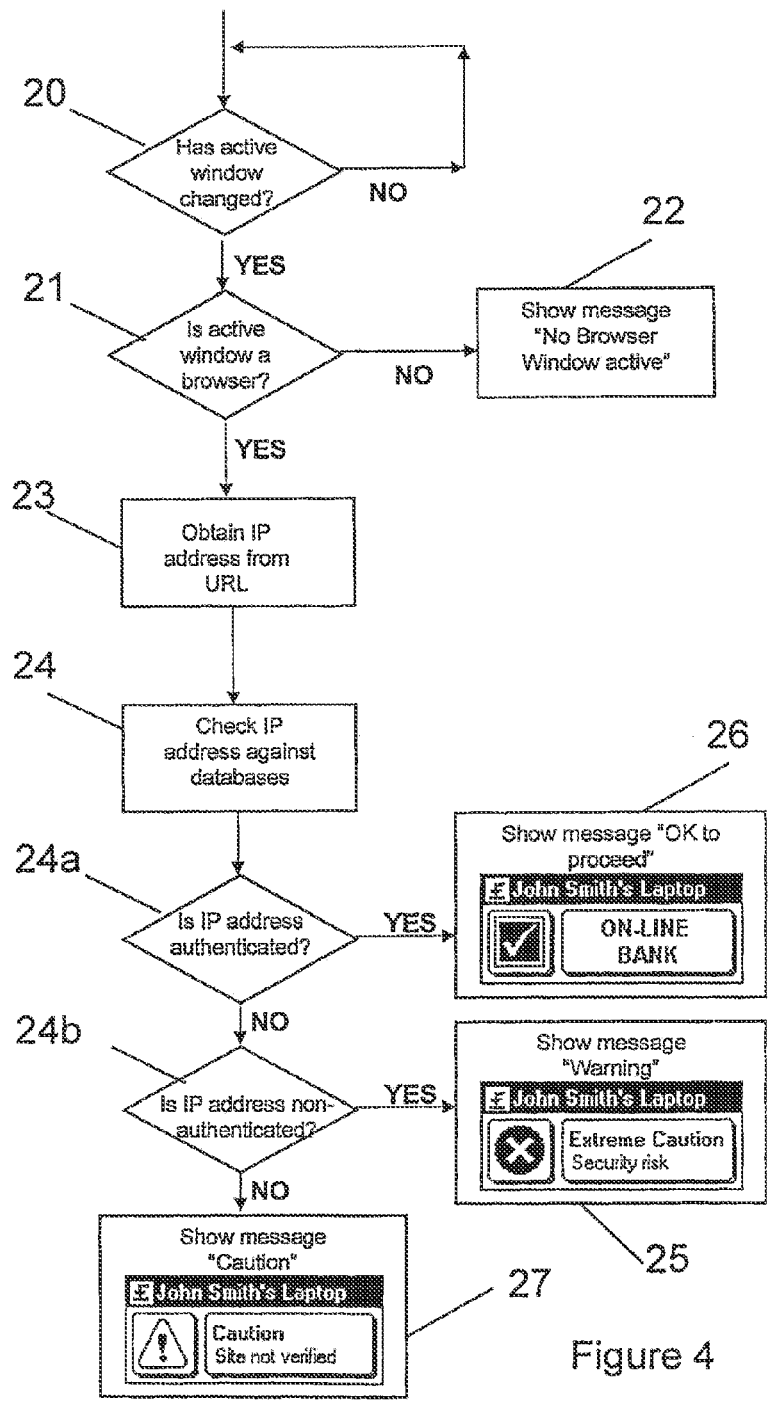
FIG. 4 is a logic flow diagram of a method performed by a client computer embodying the present invention.

Referring to FIG. 4, the server-authentication application 15, when executed, additionally checks at 20 whether the active window of the windows-based operating system has changed. In any window-based operating system, there will generally be a single active window on the computer's VDU 8, being the window on which various commands (for example "save", "print", etc.) may be initiated by the user-input device 11. Other windows may be open at the same time, whether visible on the VDU 12 or hidden behind other windows. The various windows open at any one time are usually displayed on a task bar or docking bar at an edge (e.g. the bottom) of the graphic display. An authentication check is performed whenever the active window changes. Thus, in the case of "yes" in the logic flow diagram of FIG. 4, indicating that the active window has changed, the server-authentication application 15 checks at 21 whether the new active window is a web-browser or other application capable of transferring data across the communications network 5. In the most preferred arrangement, if the active window is not a web-browser the server-authentication application may show a message 22 such as "no browser window active". In particular arrangements, this feature may be absent or may be optionally turned off by a user.

However, if the new active window is, indeed, a web-browser or other application capable of transferring data across the communication network 5, the server-authentication application 15 checks the authentication of the content-provider server 3 from which the web-browser is requesting data. This is achieved by first converting at 23 the hostname portion of the URL of the content-provider server 3 into an IP address. There are a number of ways in which this can be done and persons skilled in this art will be aware of all of these. In the simplest arrangement, the hostname portion of the URL is converted into an IP address using a DNS server.

Once the IP address of the content-provider server 3 has been obtained, the IP address is checked 24 against the client-database of non-authenticated IP addresses 16 and the client-database of authenticated IP addresses 17, if present. If the IP address appears 24a in the client-database of non-authenticated IP addresses 16, a warning is provided 25 on the VDU 12 that the user would be wise to ignore any content-data (e.g. webpage data) downloaded from the relevant content-provider server 3. If the IP address appears 24b in the client-database of authenticated IP addresses 17, an indication is provided 26 that it is fine to proceed. The indication may include a visual logo or other indicia of a content-provider such that the user is able to easily and quickly identify that the content-provider server 3 is authentic. If the IP address does not appear in either of the client-databases 16, 17, a cautionary warning is preferably provided 27 to the user. Although here shown as visible indications, any of these warnings/indications may alternatively or additionally be given audibly.

Visible messages may be conveyed in a variety of different ways. Preferably warnings or cautions are given by means of a status window, such as those shown at 25, 26 and 27 in FIG. 4 (see also FIG. 6 below), that is always on top of any windows that are open on the VDU 12. It is important that this status window should be on top so that its reporting cannot be hidden by another window. It always reports on the active window, pop-up windows, frame sets, frames or other sub-windows. The user cannot interact with a window unless it is active, so that the active window is always the dominant window that is reported, although the system could also display the status of other open windows (see FIG. 5 below) and a history of other opened windows.

Figure 5:
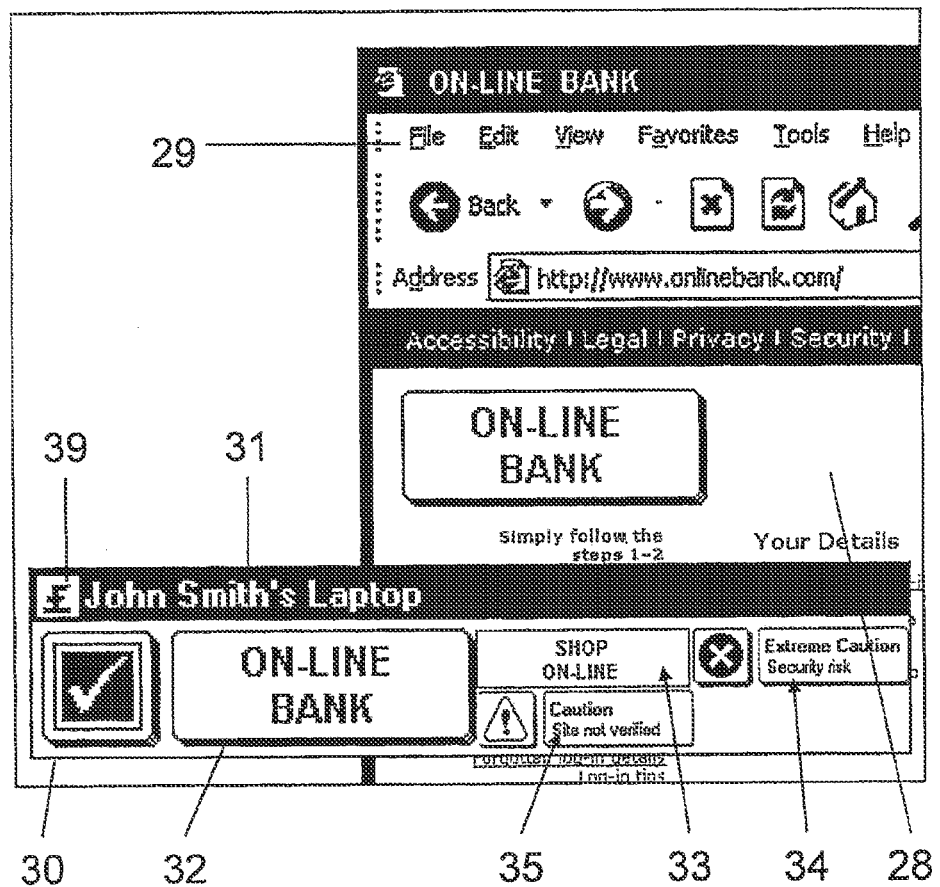
FIG. 5 shows part of a computer display illustrating an always-on-top status window.

An example of a more complex on-top status window is illustrated in FIG. 5, which shows part of a webpage 28 that is the active window, its menu bars 29 being shown at the top of the display. Always on-top status window 30 is shown on top of the active window 28. Below its title bar 31 are icons representing those windows that are open, in this example. In other examples (see for example, FIG. 6 discussed below), only the active window may have an icon. In the case shown in FIG. 5, the larger icon 32 at the left of status box 30, indicating the active window, shows the icon of OnlineBank, a legitimate website. In this example three other windows are also open, but are not active. Icons corresponding to these are shown on a smaller size in the right-hand portion of status window 30. Of these, one, 33, shows the icon of ShopOnline, a legitimate site. Of the remaining two window icons, one, 34 is suitably depicted in red, this colour and the word "warning" indicating that the site corresponding to it appears on the client-database of non-authentic IP addresses 16. Icon 35 indicates that a fourth window which is open but not active does not appear on either of the client-databases of authenticated and non-authenticated IP addresses 16, 17, and is suitably shown in yellow, indicating "Proceed with caution".

In this example, if the user clicked on to the window corresponding to the red "Warning" indication, this would then become the active window, and the system may then run through the steps of the logic flow diagram of FIG. 4. The "Warning" indication will then appear larger on the left of on-top status window 30, where the OnlineBank icon is shown in FIG. 5, the OnlineBank icon being relegated to one of the smaller icons on the right, if the related OnlineBank window remains open, and an audible warning will also be given. Alternatively, since the window concerned will have been previously checked (hence: its small icon in the right hand part of on-top status window 30 as shown in FIG. 5), the server-authentication application 13 may take account of this, and proceed as indicated above, but without first re-checking the reactivated window using the logic flow diagram of FIG. 4.

Figure 6:
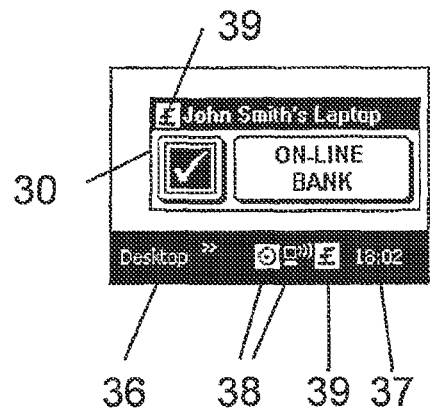
FIG. 6 shows part of a computer display illustrating part of the taskbar at the bottom of the computer display.

Warning indications may also, or alternatively, be displayed on the task bar or docking bar at the edge (e.g. bottom) of the display screen, as indicated in FIG. 6. The right hand side of a task bar 36 in a Microsoft Windows® operating system controlled computer has a clock 37 and a number of icons 38 indicating programs that are operating in the background. In some cases these icons will change depending upon the status of the program concerned. In the present system, as shown in FIG. 6, an icon 39 appears on the right hand side of the task bar and changes its status depending upon whether the active window, being a browser, has an IP address that appears in the client-database of non-authenticated IP addresses 16, the client-database of authenticated IP addresses 17 (if present), or in neither client-database. This change of status can suitably be indicated by changes in colour, the icon 39 showing green if the IP address appears in the client-database of authenticated IP addresses 17, red if the IP address appears in the client-database of non-authenticated IP addresses 16, and yellow if the IP address appears in neither of the client databases 16, 17. Suitably, an audible warning is also given in either of the latter two cases. A similar icon 39 is displayed at the left end of the title bar for the on-top status window, as seen in this Figure and also in the messages shown at 25, 26 and 27 in FIG. 4, and may also change colour in a similar fashion.

By these means the user is at all times informed as to the nature of the active window of his browser and unless he chooses to ignore the warnings given, the server-authentication application 15 will help to prevent fraudulent extraction of personal details, such as bank information that can be used illegally. It will be appreciated that the system also gives assurance to a user, when a particular content-provider server 3 is confirmed as having an IP address on the authenticated client-database 16, the content-data from that server 3 (e.g. webpage data) may be trusted.

The server-authentication application 15 may optionally be configured so that the user can only proceed after a danger warning has been expressly acknowledged by the user, e.g. by means of an optional warning pop-up window which the user has to acknowledge.

Preferably, the server-authentication application 15 determines whether the hostname of the URL of the active window relates to a content-provider server 3 external to a local network, i.e. that the hostname relates to an Internet domain-name and not, for example, to a local hostname. If the application 15 determines that the hostname of the active window relates to a local network, the application 15 preferably provides a 'Local Network' indication on the VDU 12. Additionally, if the active window is executing an application that is resident on the client computer or if the application of the active window is accessing content-data resident on the client computer 1, the server-authentication application 15 preferably displays 'Not Analysed' on the VDU; an icon or similar graphic, indicating the application that is executing in the active window, may also be displayed. Accordingly, the server-authentication application 15 continually provides a user-indication of the status of the active window.

The content-data stored on a content-provider server 3 may include a link to content-data stored on another content-provider server having a different IP address. For example, webpage data of a first content-provider may include a frame that links to information provided by a second content-provider. A typical example of this is in the use of framed advertisements within a webpage. A fraudster may use the concept of frames to provide a content-provider server that first links to content-data provided by a legitimate site (e.g. a bank) and also to content-data provided by a fraudulent site. The content-data of the fraudulent site may appear as a framed advertisement which surreptitiously monitors all data traffic between the client computer 1 and the legitimate site. Accordingly, a user may be presented with a webpage that is obtained from a legitimate site, and therefore looks and behaves as a legitimate webpage, whilst the fraudulent frame within the webpage monitors any user-authorization data entered by the user. Alternatively, a fraudulent site may include a frame to a legitimate site to show apparent authenticity, or the fraudulent site may include a frame that mimics legitimate content, e.g. the fraudulent site may include a frame that appear as a complete webpage of a legitimate site, although it is in reality a frame.

The server-authentication application 15 therefore preferably resolves and checks the IP addresses of all hostnames of content-provider servers from which content-data is retrieved by the client computer 1. In other words, the server-authentication application 15 does not only resolve and check the IP address of the hostname of the URL that appears in the active window, but also any hostnames that are embedded within the content-data retrieved from the URL. For example, if the webpage www.onlinebank.com/home.html includes a link to www.onlineshop.com/logo.html, then the server-authentication application 15 resolves and checks the IP addresses of both www.onlinebank.com and www.onlineshop.com.

It is possible that a subscriber may wish to include within its content-data an advertisement from a content-provider that is not a subscriber to the security server 4. In this instance, the IP address of the subscriber will appear in the authenticated database 7, but the IP address of the advertiser will not. Consequently, when the user visits the legitimate site of the subscriber, a warning is nevertheless provided by the server-authentication application 15. In order to prevent this from occurring, the related information 9 of the database of authenticated IP addresses 7 may include IP addresses of third-party servers that are regarded by the subscriber as legitimate for the purposes of inclusion within its content-data. The server-authentication application 15 then checks the IP address of the main hostname against the list of IP addresses 8 of the authenticated database 17. If the IP address is found within the database 17, then any hostnames that are embedded within the content-data retrieved from the main hostname are then resolved and checked against the third-party IP addresses stored in the related-information 9.

A content-provider server 3 may store both non-fraudulent and fraudulent content-data. In particular, a content-provider server 3 may host different websites. For example, the content-provider server 3, www.freewebsite.com, may host the website of John, www.freewebsite.com/John/home.html, and the website of Peter, www.freewebsite.com/Peter/home.html. Whilst John provides a legitimate website, the website provided by Peter is a spoof website. Since the hostname of both websites is the same, the resolved IP address of each website will also be the same. Consequently, both websites are treated equally by the server-authentication application 15. The legitimate website provided by John may therefore be reported as a fraudulent site or, alternatively, the spoof site provided by Peter may be reported as a legitimate site. In order to prevent this situation from occurring, the database of non-authenticated IP addresses 6 and the database of authenticated IP addresses 7 preferably store not only IP addresses but also the URL or part of the URL associated with the IP address. For example, if the IP address of www.freewebsite.com is 121.202.327.75, the database of non-authenticated IP addresses 6 might store the IP address 121.202.327.75 and the path '\Peter' and/or the filename '\Peter\home.html', whilst the database of authenticated IP addresses 7 might store 121.202.327.75 and '\John' and/or '\John\home.html'. The server-authentication application 15 is then operable to check both the IP address and also at least part of the URL against the corresponding client-databases 16, 17. Only if both the IP address and at least part of the URL appear in the client-databases 16, 17 is a warning 25 or indication 26 provided.

The database of non-authenticated IP addresses 6, the client-database of non-authenticated IP addresses 16, and any fragment 18 may store only the domain name, URL or part of a URL of a particular content-provider server 3. In this case, the IP address of the domain is stored in the database 6,16 or fragment 18 as a series of asterisks (i.e. *.*.*.*) or some other artificial IP address (e.g. 999.999.999.999), which the server authentication application 15 uses to identify a server as having no specific or fixed IP address. For example, the website www.falsewebsite.com may change its IP address frequently in order to avoid detection. If the IP address of a content-provider server 3 is not found in the client-database of non-authenticated IP addresses 16, the domain name, URL or part URL of the content-provider server 3 is then compared against each of the entries in the client-database 16 having an artificial IP address. If the domain name, URL or part URL of the content-provider server 3 appears in the client database 16, a suitable warning is provided 25. Alternatively, the comparison of domain names, URL or part URL may be carried out before the comparison of IP addresses. By storing the domain name, URL or part URL of content-provider servers 3 that employ frequently-changing IP addresses, the server authentication application 15 is still able to identify fraudulent content providers.

Figure 7:
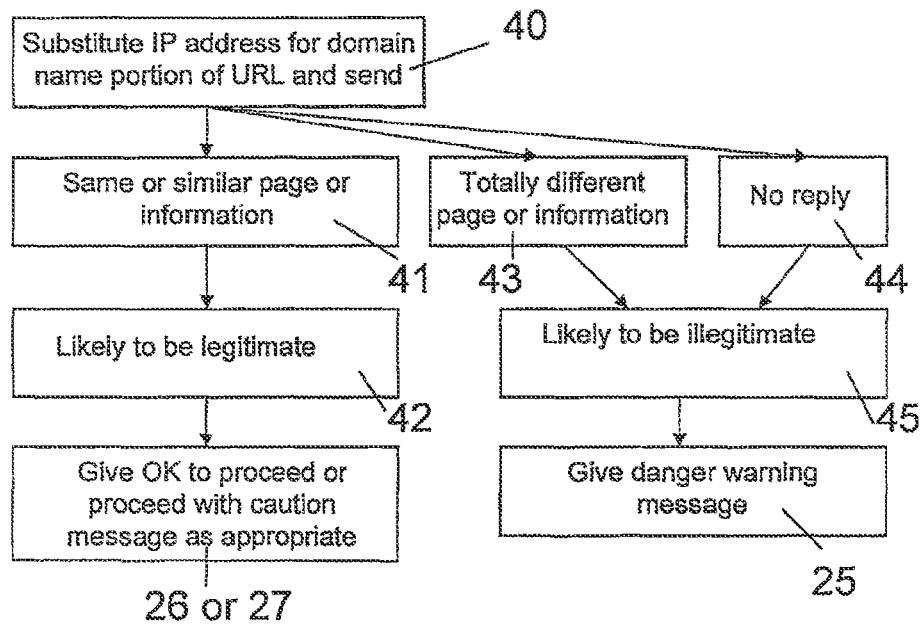
FIG. 7 is a logic flow diagram of a further method performed by a client computer embodying the present invention.

In the most preferred arrangement, the server-authentication application 15 also guards against IP-address spoofing when the IP address, having been checked, may appear on the authenticated client-database 17 or on neither of the authenticated and non-authenticated client-databases 16, 17, and yet the content-data (e.g. webpage data) may still emanate from a fraudulent source. A sophisticated fraudster can configure a content-provider server 3 to send content-data that appears to emanate from a different IP address to the one it actually does come from. To overcome this, in the most preferred arrangement, when the check carried out at 24 shows either that the IP address of the active window appears on the client database of authenticated IP addresses 17, or that the IP address of the active window does not appear on either of the client-databases 16, 17, and so could still possibly be a legitimate site, a further short routine is performed, as illustrated in FIG. 7.

The apparently authenticated IP address or the IP address that does not appear on either client-database 16, 17 is substituted at step 40 for the hostname portion of the URL, and a request for the content-data of the URL is sent. Thus, for example, if the web-browser receives content-data (e.g. a webpage data) claiming to be from www.mybank.com/customer/data/home.html and the server-authentication application 15 ascertains at 23 in the flow diagram of FIG. 4 that the IP address of www.mybank.com is, say, 123.456.789.100, then at step 40 the server-authentication application 15 sends a request for the content-data of http://123.456.789.100/customer/data/home.html. The same or similar content-data should be returned. If it is, at step 41, then the implication 42 is that the site is likely to be legitimate and then depending upon whether the IP address appears in the client-database of authenticated IP addresses 17 or does not appear in either client-database 16,17, the "OK to proceed" indication 26 or the "Proceed with caution" indication 27 will be displayed.

However, if different content-data is provided (i.e. if the webpage appears different) as a result of the resending request 40 as indicated at 43, or if no reply is provided 44, then the server-authentication application 15 draws the implication at step 45 that the content-provider server 3 is likely to be illegitimate, notwithstanding that the original apparently derived IP address at step 23 may have indicated an IP address that appeared on the authenticated client-database 17 (or did not appear on either client-database 16,17 and so could possibly be legitimate). Accordingly, in event 45, rather than displaying either the "OK to proceed" indication 26 or the "Proceed with caution" indication 27, the clear "Warning" indication 25 is displayed.

Additionally, or alternatively, the server-authentication server 15 may alert the user to spoofing by displaying the actual hostname or URL, as well as the IP address, of the content-data or content-provider server 3 such that the user can immediately identify whether the actual hostname or URL corresponds to that which appears in the active window.

In the above-described embodiment, the server-authentication application 15 receives (e.g. downloads) from the security server 4 the entire database of non-authenticated IP addresses 6 and also the entire database of authenticated IP addresses 7. As the number of subscribers to the service provided by the security server 4 increases, the size of the authenticated database 7 will naturally increase. With sufficient numbers of subscribers, the size of the authenticated database 7 may become excessively large such that too much time is spent by the client computer 1 in receiving the database 7. Moreover, it is unlikely that a user will download content-data from each and every one of the subscribers having IP addresses stored in the database 7. Accordingly, in an alternative embodiment as illustrated in FIG. 8, the database of authenticated IP addresses 7 comprises a plurality of fragments 18, each fragment 18 corresponding to a particular domain 19 and storing IP address 8 associated with the domain 19. Related information 9, such as the date on which the fragment was created, the subscriber that provided the fragment, URL links etc., may again be additionally stored, with each fragment 18 having respective related information 9.

The database of non-authenticated IP addresses 6, like that of the authenticated database 7, may also comprise a plurality of fragments 18, each fragment 18 corresponding to a particular domain 19 and storing IP address 8. Preferably, each fragment 18 comprises both a list of non-authenticated IP addresses and a list of authenticated IP addresses 8. Consequently, a content-provider is able to provide a fragment 18 that stipulates which sites (i.e. IP addresses) it considers to be genuine and which sites is considers to be fraudulent. When the fragment 18 is received (e.g. downloaded) by the server-authentication application 15, the relevant portions of the fragment (e.g. the lists of non-authenticated and authenticated IP addresses) are extracted and added to the client databases 16,17.

In this alternative embodiment, the server-authentication application 15 includes instructions to determine the hostname of the URL of the active window. The application 15 then compares the hostname against the client-database of authenticated IP addresses 17. If a fragment corresponding to the hostname is found in the client-database 17, the IP address of the hostname is resolved and compared against the IP addresses listed for that fragment, in the manner described above.

If, however, no fragment 18 corresponding to the hostname can be found in the client-database of authenticated IP addresses 17 (e.g. if no fragments having the same domain as that of the hostname are found), then preferably a similar search is made of the server-database of authenticated IP addresses 7. In particular, the server-authentication application 15 establishes a connection with the security server 4 and compares the hostname of the content-provider server 3 against the server-database fragments. If a fragment 18 corresponding to the hostname is found in the server-database of authenticated IP addresses 7, the relevant fragment is delivered to the client computer 1. The IP address of the hostname is then resolved and compared against the IP addresses listed in the fragment, in the manner described above. The received fragment is then added to the existing client-database 17 for future use. If no fragment 18 corresponding to the hostname of the content-provider server 3 can be found in the server-database fragments, the server-authentication application 15 provides as an indication (e.g. the "Proceed with caution") that the authenticity of the content-provider server 3 could not be verified.

Rather than comparing the hostname of the active window URL against fragments of the client-database 17, the client computer 1 may alternatively store a database of visited servers in memory 13. The database of visited servers stores a list of hostnames of content-provider servers 3 that have previously been accessed by the client computer 1, or alternatively a list of domains of content-provider servers 3 that have been accessed. The hostname of the URL is then compared against the database of visited servers. If a match is found, the IP address of the hostname is resolve and compared against the IP addresses listed in the client-database 17 in the manner described above. If, however, a match is not found, then the hostname is added to the database of visited servers by the server-authentication application 15. The application 15 then establishes a connection with the security server 4 and compares the hostname against the server-database of authenticated IP addresses 7. If a fragment 18 corresponding to the hostname is found in the server-database of authenticated IP addresses 7, the relevant fragment is delivered to the client computer 1, whereupon the received fragment is added to the existing client-database 17. The IP address of the hostname is then resolved and compared against the IP addresses listed in the client-database 17 in the manner described above.

Where the client-database of authenticated IP addresses 17 is stored as fragments 18, it is possible for the authenticated client-database 17 to become outdated. For example, once the fragment for 'onlinebank.com' is added to the client-database 17, is it possible for the server-authentication application 15 to re-authenticate the site 'onlinebank.com' at a later date without having to rely upon the security server 4. In order to prevent the authenticated client-database 17 from becoming outdated, the server-authentication application 15 may periodically refresh fragments 18, i.e. retrieve once again the fragments 18 from the security server 4. The related-information 9 associated with each fragment may include a creation or expiry date, which is used by the server-authentication application 15 to determine when to refresh the fragment or, alternatively, delete the fragment from the client-database 17. Similarly, where the client computer 1 stores a database of visited servers, each entry in the database may include a creation or expiry date, which is again used by the server-authentication application 15 to determine when to refresh the entry and corresponding fragment or, alternatively, delete the entry from the database.

In a further embodiment, fragments 18 associated with a particular domain may be stored on a content-provider server 3 of a subscriber. For example, the fragment for 'onlinbank.com' may be stored on a server provided by OnlineBank in addition to or rather than the security server 4. In this embodiment, the server-authentication application 15 then receives the relevant fragment from the content-provider server 3 rather than the security server 4. Preferably, the relevant fragment is received (e.g. downloaded) from the content-provider server 3 in response to the client computer 1 requesting content-data from the content-provider server 3, e.g. when attempting to view webpage data. Similarly, the database of non-authenticated IP addresses 6 may be additionally or exclusively stored on a server of an assured organisation. Indeed, the server-authentication application 15 may present the user with the option of receiving (e.g. downloading) fragments/databases exclusively from the security server 4 or additionally from the server of the relevant content-provider/organisation if the fragment/database is unavailable from security server 4.

Although each fragment 18 may comprise a list of non-authenticated IP addresses in addition to a list of authenticated IP addresses 8, the fragment 18 and therefore the list of non-authenticated IP addresses list is obtained only after receiving (e.g. downloading) the fragment from the content-provider server 3. It is therefore possible that the client-database of non-authenticated IP addresses 16 will not include information on known fraudulent sites until such time as the content-provider server 3 has been visited and the fragment 18 obtained. Accordingly, the server-authentication application 15 preferably also receives from the security server 4, or other assured organisation, the database of non-authenticated IP addresses 6 at regular intervals in addition to any fragments that may have been received. Rather than receiving the entire database 6, the server-authentication application 15 may check regularly for updates that become available. As already noted, the server-authentication application 15 preferably provides the user with the opportunity to receive a new, updated or refreshed database 6 from the security server 4 at periodic intervals.

The databases 6,7, as well as any fragments 18, are preferably encrypted using a proprietary 256-bit encryption having keys derived from the domain name of the server 3,4 storing the database 6,7 or fragment 18 and the domain name from which the database 6,7 or fragment 18 is received by the server-authentication application 15. Accordingly, the server-authentication application 15, upon decrypting the received databases 16,17 or fragments 18, is able to determine whether the databases 16,17 or fragments were received from the correct source and that the data contained therein is self-consistent. Additionally, in the case of fragments 18, the server-authentication application 15 is able to determine that the received fragment contains information corresponding to the correct domain. Even if a fraudster were to download an encrypted database 6,7 or fragment 18 and, with significant computing power, decrypt the database 6,7 or fragment 18 with the intention of inserting false IP addresses, the fraudster would not know the relevant key to re-encrypt the database 6,7, or fragment 18 in order to, for example, place the fake encrypted database 6,7 or fragment 18 on a spoof server. Encryption therefore prevents a spoof site creating an apparently valid database 6,7, or fragment 18.

In addition to encrypting the contents of the fragments 18, the filename of each fragment 18 may also be encrypted. For example, the fragment 18 corresponding to the domain 19 onlinebank.com may be stored on the security server 4 or a specific content-provider server 3 as a file called hqofmnn9hc64pxvk.xml, which has no apparent relation to the actual domain name. The filename of the fragment 18 is preferably encrypted using a first key based upon the domain 19 to which the fragment 18 relates (e.g. onlinebank.com) and a second key based upon the domain of the security server 4 or the specific content-provider server 3. The filename of the fragment 18 will therefore be different when stored on different servers. In order to retrieve a fragment 18, the server-authentication application 15 first resolves the fragment filename using the domain 19 to which the fragment 18 relates and the domain of the server 3,4 storing the fragment 18. The server-authentication application 15 then retrieves (e.g. downloads) from the server 3,4 a file having the resolved filename. Since the filename of the fragment depends upon the domain of the server storing the fragment, a fragment copied from a first server to a second server (e.g. from the security server 4 to a fraudulent server) will not be found by the server-authentication application 15.

The server-authentication application 15 may store a history database of recently visited sites, i.e. a list of content-provider servers 3 from which content data has recently been retrieved by the client computer 1. By way of example, the history database may include a list of all content-provider servers 3 that have been visited in the last month. When the server-authentication application 15 is idle, the application 15 may retrieve fragments 18 corresponding to those content-provider servers 3 that are listed in the history database. In this manner, the fragments 18 of content-provider servers 3 that are likely to be revisited are kept up-to-date such that no noticeable delay is observed by the server-authentication application 15 when the content-provider servers 3 are revisited. The history database preferably includes information regarding the date and/or time on which the fragment 18 corresponding to a particular content-provider server 3 was last retrieved or updated. The server-authentication application 15 then retrieves only those fragments 18 where the authenticity of the fragment 18 has timed-expired.

The server-authentication application 15, which is the software necessary to configure a client computer 1 to operate in the manner described above and to provide security against phishing over the communications network 5, may be provided as a single computer program or suite of computer programs, which may be provided on a computer-readable data storage device, such as a floppy disk or a CD/DVD. Alternatively, the computer program or suite of computer programs may be made available for download over the communication network 5 from the security server 4 (see FIG. 1), or from a trusted content-provider server 3, such as a bank, licensed to provide the software.

To prevent fraudsters spoofing the server-authentication software, the user is requested to enter a unique identifier upon installing the software. The unique identifier entered by the user is then encrypted, preferably using a key particular to the user's copy of the server-authentication software, and stored (e.g. as a file) in the memory 13 of the client computer 1. The server-authentication application 15, when executed, decrypts and displays the unique identifier on the VDU 12, e.g. on the title bar of the server-authentication application 15. If the server-authentication software were to be replaced (e.g. by a fraudulent copy), the encryption key would be unknown and accordingly an incorrect unique identifier would be displayed by the application 15 on the VDU. Accordingly, the user is provided with an indication if the server-authentication software has been changed.

Banks, financial institutions and other e-commerce or similar content-providers which provide services and/or information over the Internet and which rely upon user-authorisation data (e.g. personal details of a user) or wish to assure users of the validity of their webpages and any information thereby conveyed may register their IP addresses with the provider of the security server 4 to be included in the database 7 of authenticated IP addresses.

Provision may also be made for users themselves to enter frequently used websites, by their URLs converted into IP addresses, or by the IP addresses themselves, into the authenticated client-database 17 maintained on the client computer 1 so as to avoid unnecessary "Caution" warnings being displayed simply because the content-provider of an otherwise legitimate website may choose not to subscribe to the service provided by the security server 4.

Although the invention has been described hereinabove in terms of databases being stored on a client computer 1 both for authenticated IP addresses 17 and for non-authenticated IP addresses 16, and these databases being used to determine whether the IP address of a particular website appeared on one of these two databases or on neither, with appropriate messages or other indications being conveyed to the user in each of these three circumstances, this is not always necessary.

For example, only a database of authenticated IP addresses 17 may be stored, and in that case, the server-authentication application 15 is only able to give assurance that a website may be trusted when its IP address is found in that database (and, if the check against address spoofing feature is included, the address is additionally shown not to have been spoofed). Equally well, only a database of non-authenticated IP addresses 16 may be stored, and in that case, the server-authentication application 15 is only able to give a clear danger warning when the IP address of a particular website appears in this database or (if the check against address spoofing feature is also included) if the address is shown to have been spoofed.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

What is claimed is:

1. A computer-implemented method of authenticating a content-provider server computer coupled to a computer network and having an IP address, the method comprising:
coupling a client computer to the computer network;
in the client computer, storing a client-database of authenticated IP addresses and a client-database of non-authenticated IP addresses;
in the client computer, detecting that a user of the client computer has requested data from a website associated with a domain name of the content-provider server computer;
downloading a fragment of a server-database of IP addresses from a remote server computer to the client computer, the fragment corresponding to the domain name of the content-provider server computer and including one or more authenticated IP addresses and one or more non-authenticated IP addresses associated with the domain name of the content-provider server computer;
appending the one or more authenticated IP addresses and the one or more non-authenticated IP addresses of the fragment to at least one of the client-database of authenticated IP addresses and the client-database of non-authenticated IP addresses to update the client-database of authenticated IP addresses and the client-database of non-authenticated IP addresses;
obtaining, by the client computer, the IP address of the content-provider server computer after detecting that the user has requested data from the website associated with the domain name of the content-provider server computer;
comparing the IP address of the content-provider server computer against the updated client-database of authenticated IP addresses and the updated client-database of non-authenticated IP addresses; and
providing a visual indication to the user of the client computer that the IP address of the content-provider server computer is one of the one or more authenticated IP addresses, one of the one or more non-authenticated IP addresses, or neither.

2. The method of claim 1, wherein downloading the fragment comprises:
requesting from the remote server computer a copy of the fragment; and
receiving from the remote server computer the requested copy of the fragment.

3. The method of claim 2, wherein the fragment is stored on the remote server computer as a file having a filename that is unique to the domain name of the content-provider server computer and requesting the copy of the fragment from the remote server computer comprises requesting the file having the filename that is unique to the domain name of the content-provider server computer.

4. The method of claim 2, wherein the fragment is stored on the remote server computer as a file having a filename that is unique to both the domain name of the content-provider server computer and a domain name of the remote server computer on which the fragment is stored, and
  requesting the copy of the fragment from the remote server computer comprises requesting the file having the filename that is unique to both the domain name of the content-provider server computer and the domain name of the remote server computer on which the fragment is stored.

5. The method of claim 1, wherein the content-provider server computer is a first content-provider server computer and has a hostname, and the method further comprises:
  obtaining first data from the first content-provider server computer having the hostname;
  resolving the IP address of the hostname;
  obtaining second data from a second content-provider server computer having the resolved IP address, the second content-provider server computer being the same as or different from the first content-provider server computer;
  comparing the first data and the second data; and
  providing an indication that the first data and the second data are identical or non-identical.

6. The method of claim 1, wherein the content-provider server computer has a URL and the fragment includes one or more URLs or portions of URLs associated with each IP address stored by the fragment, and the method further comprises:
  comparing at least a portion of the URL of the content-provider server computer against the URLs or portions of the URLs of the fragment that are associated with the IP address of the content-provider server computer; and
  providing an indication that the IP address and the portion of the URL of the content-provider server computer is included in or excluded from the fragment.

7. A client computer connectable to a content-provider server computer over a communications network, wherein the client computer is operable to:
  store a client-database of authenticated IP addresses and a client-database of non-authenticated IP addresses;
  detect that a user of the client computer has requested data from a website associated with a domain name of the content-provider server computer;
  download a fragment of a server-database of IP addresses from a remote server computer, the fragment corresponding to the domain name of the content-provider server computer and including one or more authenticated IP addresses and one or more non-authenticated IP addresses associated with the domain name;
  append the IP addresses of the fragment to at least one of the client-database of authenticated IP addresses and the client-database of non-authenticated IP addresses to update the client-database of authenticated IP addresses and the client-database of non-authenticated IP addresses;
  obtain an IP address of the content-provider server computer after detecting that the user has requested data from the website associated with the domain name of the content-provider server computer;
  compare the IP address of the content-provider server computer against the updated client-database of authenticated IP addresses and the updated client-database of non-authenticated IP addresses; and
  provide a visual indication to the user of the client computer that the IP address of the content-provider server computer is one of the one or more authenticated IP addresses, one of the one or more non-authenticated IP addresses, or neither.

8. The client computer of claim 7, wherein the client computer is operable to download the fragment by:
  requesting fragment data from the content-provider server computer, and
  obtaining the fragment in response to requesting the fragment data from the content-provider server computer.

9. The client computer of claim 7, wherein the client computer is operable to:
  determine whether data has previously been requested from the content-provider server computer; and
  obtain the fragment if data has not previously been requested from the content-provider.

10. The client computer of claim 7, wherein the client computer is operable to:
  obtain data from the content-provider server computer that includes a link to a different content-provider server computer;
  compare the IP address of the different content-provider server computer against the IP addresses of the fragment; and
  provide an indication that the IP address of the different content-provider server computer is included or excluded from the IP addresses of the fragment.

11. A computer-implemented method of authenticating a content-provider server computer coupled to a computer network and having an IP address, the method comprising:
  coupling a client computer to the computer network;
  in the client computer, storing a client-database of authenticated IP addresses and a client-database of non-authenticated IP addresses;
  in the client computer, determining a domain name of the content-provider server computer;
  requesting, by the client computer, a fragment of a server-database of IP addresses from a remote server computer, the fragment being stored on the remote server computer as a file having a filename that is unique to both the domain name of the content-provider server computer and a domain name of the remote server computer on which the fragment is stored, wherein (a) the filename of the fragment is encrypted using encryption keys derived from the domain name of the content-provider server computer and the domain name of the remote server computer on which the fragment is stored, and (b) requesting of the fragment from the remote server computer comprises requesting the file having the encrypted filename that is unique to both the domain name of the content-provider server computer, and a domain name of the remote server computer on which the fragment is stored;
  receiving, by the client computer, the fragment from the remote server computer, the fragment including one or more authenticated IP addresses and one or more non-authenticated IP addresses associated with the domain name of the content-provider server computer;
  appending the one or more authenticated IP addresses and the one or more non-authenticated IP addresses of the fragment to at least one of the client-database of authenticated IP addresses and the client-database of non-authenticated IP addresses to update the client-database of authenticated IP addresses and the client-database of non-authenticated IP addresses;
  comparing the IP address of the content-provider server computer against the updated client-database of authenticated IP addresses and the updated client-database of non-authenticated IP addresses; and providing a visual indication to a user of the client computer that the IP address of the content-provider server computer is one of the one or more authenticated IP addresses, one of the one or more non-authenticated IP addresses, or neither.

12. The method of claim 11, wherein the content-provider server computer is a first content-provider server computer and has a hostname, and the method further comprises:

obtaining first data from the first content-provider server computer having the hostname;

resolving the IP address of the hostname;

obtaining second data from a second content-provider server computer having the resolved IP address, the second content-provider server computer being the same as or different from the first content-provider server computer;

comparing the first data and the second data; and providing an indication that the first data and the second data are identical or non-identical.

13. The method of claim 11, wherein the content-provider server computer has a URL and the fragment includes one or more URLs or portions of URLs associated with each IP address stored by the fragment, and the method further comprises:

comparing at least a portion of the URL of the content-provider server computer against the URLs or portions of the URLs of the fragment that are associated with the IP address of the content-provider server computer; and providing an indication that the IP address and the portion of the URL of the content-provider server computer is included in or excluded from the fragment.

14. A client computer connectable to a content-provider server computer over a communications network, wherein the client computer is operable to:

store a client-database of authenticated IP addresses and a client-database of non-authenticated IP addresses;

determine a domain name of the content-provider server computer;

request a fragment of a server-database of IP addresses from a remote server computer, the fragment being stored on the remote server computer as a file having a filename that is unique to both the domain name of the content-provider server computer and a domain name of the remote server computer on which the fragment is stored, wherein (a) the filename of the fragment is encrypted using encryption keys derived from the domain name of the content-provider server computer and the domain name of the remote server computer on which the fragment is stored, and (b) requesting of the fragment from the remote server computer comprises requesting the file having the encrypted filename that is unique to both the domain name of the content-provider server computer, and a domain name of the remote server computer on which the fragment is stored;

receive the fragment from the remote server computer, the fragment including one or more authenticated IP addresses and one or more non-authenticated IP addresses associated with the domain name of the content-provider server computer;

append the IP addresses of the fragment to at least one of the client-database of authenticated IP addresses and the client-database of non-authenticated IP addresses to update the client-database of authenticated IP addresses and the client-database of non-authenticated IP addresses;

compare the IP address of the content-provider server computer against the updated client-database of authenticated IP addresses and the updated client-database of non-authenticated IP addresses; and provide a visual indication to a user of the client computer that the IP address of the content-provider server computer is one of the one or more authenticated IP addresses, one of the one or more non-authenticated IP addresses, or neither.

15. The client computer of claim 14, wherein the client computer is operable to:

request data from the content-provider server computer;

determine whether data has previously been requested from the content-provider server computer; and download the fragment if data from the content-provider has not previously been requested.

16. The client computer of claim 14, wherein the client computer is operable to:

obtain data from the content-provider server computer that includes a link to a different content-provider server computer;

compare the IP address of the different content-provider server computer against the IP addresses of the fragment; and provide an indication that the IP address of the different content-provider server computer is included or excluded from the IP addresses of the fragment.

* * * * *